(12) United States Patent
Kiyoshima et al.

(10) Patent No.: US 6,333,417 B1
(45) Date of Patent: Dec. 25, 2001

(54) METHOD FOR PRODUCING HEXAHYDRO-2-OXO-1H-THIENO[3,4-D]IMIDAZOLE-4-PENTANOIC ACID

(75) Inventors: Yujiro Kiyoshima; Yasunobu Miyamoto, both of Oita (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/471,251

(22) Filed: Dec. 23, 1999

(30) Foreign Application Priority Data

Dec. 24, 1998 (JP) .................................. 10-367060

(51) Int. Cl.$^7$ ................................................ C07D 495/04
(52) U.S. Cl. ................................................ 548/303.7
(58) Field of Search .......................... 548/303.7

(56) References Cited

U.S. PATENT DOCUMENTS 4,537,973 * 8/1985 Takahashi et al. .................... 548/303

FOREIGN PATENT DOCUMENTS

| | | |
|---|---|---|
| 084377 * | 7/1983 | (EP) . |
| 638954B | 2/1988 | (JP) . |
| WO9843979 | 10/1998 | (WO) . |

* cited by examiner

*Primary Examiner*—Laura L. Stockton
(74) *Attorney, Agent, or Firm*—Birch, Stewart, Kolasch & Birch, LLP

(57) ABSTRACT

There is disclosed a process for producing hexahydro-2-oxo-1H-thieno[3,4-d]imidazole-4-pentanoic acid of the formula (2):

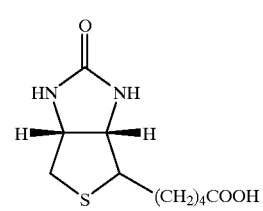

(2)

which is characterized by contacting a compound of the formula (1):

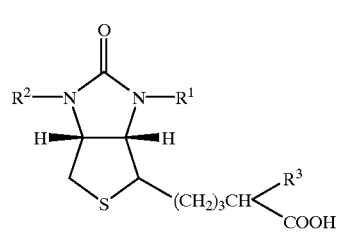

(1)

wherein $R^1$ and $R^2$ represent a hydrogen atom or a benzyl group, but $R^1$ and $R^2$ do not simultaneously represent a hydrogen atom, and $R^3$ represents a hydrogen atom or a carboxyl group, with sulfuric acid in the presence of an aromatic hydrocarbon.

7 Claims, No Drawings

METHOD FOR PRODUCING HEXAHYDRO-2-OXO-1H-THIENO[3,4-D]IMIDAZOLE-4-PENTANOIC ACID

FIELD OF THE INVENTION

The present invention relates to a method for producing hexahydro-2-oxo-1H-thieno[3,4-d]imidazole-4-pentanoic acid.

DESCRIPTION OF THE RELATED ART

Hexahydro-2-oxo-1H-thieno[3,4-d]imidazole-4-pentanoic acid is also called vitamin H (biotin), a compound effective for promoting growth, preventing and curing skin diseases, and the like, and used as a feed additive, and the like.

As a method for producing such hexahydro-2-oxo-1H-thieno[3,4-d]imidazole-4-pentanoic acid, there is disclosed a method in which hexahydro-2-oxo-1,3-dibenzylthieno[3,4-d]imidazole-4-pentanoic acid is treated with alkanesulfonic acid such as methanesulfonic acid (Japanese Patent Application Publication (JP-B) No. 63-8954). However, this method is not always industrially and economically satisfactory since a rather large amount of expensive alkanesulfonic acids is used, and recovery of the used alkanesulfonic acid is a cumbersome process.

SUMMARY OF THE INVENTION

An object of the present Invention is to provide a industrially advantageous method for producing hexahydro-2-oxo-1H-thieno[3,4-d]imidazole-4-pentanoic acid without using expensive alkanesulfonic acid.

The present invention provides a method for producing hexahydro-2-oxo-1H-thieno[3,4-d]imidazole-4-pentanoic acid of the formula (2):

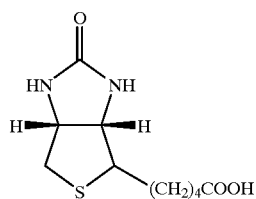

(2)

which method comprises contacting a compound of the formula (1):

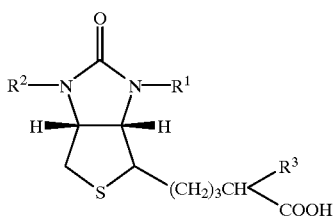

(1)

wherein $R^1$ and $R^2$ represent a hydrogen atom or a benzyl group, provided that $R^1$ and $R^2$ do not simultaneously represent a hydrogen atom, and $R^3$ represents a hydrogen atom or a carboxyl group, with sulfuric acid in the presence of an aromatic hydrocarbon.

DESCRIPTION OF THE PREFERRED EMBODIMENTS

The present invention will be illustrated in detail below.

In the general formula (1), $R^1$ and $R^2$ represent a hydrogen atom or a benzyl group, but $R^1$ and $R^2$ do not simultaneously represent a hydrogen atom, and $R^3$ represents a hydrogen atom or a carboxyl group.

Examples of the compound represented by such general formula (1) include hexahydro-2-oxo-1,3-dibenzylthieno[3,4-d]imidazole-4-pentanoic acid, hexahydro-2-oxo-1-benzyl-3H-thieno[3,4-d]imidazole-4-pentanoic acid, hexahydro-2-oxo-1,3-dibenzylthieno[3,4-d]imidazole-4-(4-hydroxycarbonyl)pentanoic acid and the like. The compound of the formula (1) theoretically has optical isomers, and any of the optically active isomers which include an isomer having the same stereochemistry as D-biotin with respect to a thieno[3,4-d]imidazole moiety, racemates or a mixture containing at least one optical isomer in excess can be used in the present invention.

The amount of sulfuric acid is usually 1 mol or more per mol of the compound of the formula (1). The upper limit thereof is not particularly restricted, however, it is preferably 20 moles, and more preferably 10 moles per mole of the compound of the formula (1). The concentration of sulfuric acid is preferably 90% by weight or more in view of yield.

Examples of the aromatic hydrocarbon include:

an alkylbenzene which is substituted with 1 to 5 ($C_1$–$C_3$) alkyl group(s) such as toluene, xylene, mesitylene, 1,2,4-trimethylbenzene, durene, pentamethylbenzene, cymene, cumene, diisopropylbenzene and the like; and an alkylnaphtalene which is substituted with 1 to 7 ($C_1$–$C_3$)alkyl group(s) such as methylnaphtalene, dimethylnaphthalene, trimethylnaphthalene, diisopropylnaphthalene and the like; and a mixture containing the above-described alkylbenzenes and/or the alkylnaphthalene.

The alkylbenzenes are preferred, and mesitylene is particularly preferred among them.

The amount of such aromatic hydrocarbon is 2 moles or more, preferably 5 moles or more per mol of the compound of the formula (1). The upper limit thereof is not particularly restricted, and it is preferably 30 moles, more preferably 20 moles per mol of the compound of formula(1).

The compound of the formula (1) is usually contacted with sulfuric acid in the presence of the aromatic hydrocarbon usually at 50° C. or more, preferably 70° C. or more, more preferably 90° C. or more and up to usually 120° C., preferably 100° C.

After completion of the treatment, the desired compound of the formula (2) can be usually obtained by a conventional post-treatment. Preferably, a sulfuric layer containing hexahydro-2-oxo-1H-thieno[3,4-d]imidazole-4-pentanoic acid and an aromatic hydrocarbon layer in the reaction mixture are usually separated. A hydrophobic organic solvent such as toluene, xylene and the like may also be added to wash the sulfuric acid layer, if necessary.

The separated sulfuric acid layer containing hexahydro-2-oxo-1H-thieno[3,4-d]imidazole-4-pentanoic acid is usually mixed with water by pouring it into water or by adding water thereto to give a crude crystal of the desired compound. The mixing of the sulfuric acid layer with water can be conducted in the presence of a lower carboxylic acid such as $C_1$–$C_2$ carboxylic acid(e.g., formic acid or acetic acid), which results in smooth precipitation of the crystal of the desired compound, which has good filtrability. The lower carboxylic acid may be added to the sulfuric acid layer or to the water. Alternatively, the lower carboxylic acid may be added when the compound of the formula (1) is contacted with sulfuric acid in the presence of the aromatic hydrocarbon.

The amount of the lower carboxylic acid to be used is not limited, but is usually 10 moles or less per mol of the compound of the formula (1) from a practical view point.

Alternatively, the crude crystal of the desired compound may also be obtained by mixing the sulfuric acid layer with an aqueous alkaline solution followed by activated carbon treatment and crystal precipitation with an acid. Examples of the alkaline solution include those of sodium hydroxide and potassium hydroxide. Examples of the acid used to precipitate the crystals of the desired compound of the formula (2) include a mineral acid such as hydrochloric acid or sulfuric acid, and a lower carboxylic acid such as formic acid or acetic acid. The presence of the lower carboxylic acid in the precipitation of the crystals of the desired compound with a mineral acid is useful for smooth precipitation of the crystals of the desired compound, which have good filtrability.

The crystals obtained by the above-described methods can be further purified by recrystalization in water or the procedure described in the above paragraph may be repeated in a similar manner.

Used aromatic hydrocarbons in the separated aromatic hydrocarbon layer can be recovered by a usual treatment such as distillation and the like, and the recovered aromatic hydrocarbons can be used in the present process again.

When an optically active compound of the formula (1) is used, an optically active hexahydro-2-oxo-1H-thieno[3,4-d]imidazole-4-pentanoic acid, for example, D-biotin can be obtained.

According to the method of the present invention, hexahydro-2-oxo-1H-thieno[3,4-d]imidazole-4-pentanoic acid can be easily obtained from a compound of the formula (1) using inexpensive sulfuric acid. Therefore, this method is advantageous industrially and economically.

EXAMPLES

The following examples further illustrate the present invention in more detail, but do not limit the scope of the invention. In these examples, the purities of hexahydro-2-oxo-1,3-dibenzylthieno[3,4-d]imidazole-4-pentanoic acid and hexahydro-2-oxo-1H-thieno[3,4-d]imidazole-4-pentanoic acid were measured by high performance liquid chromatography.

Example 1

A mixture composed of 100.46 g (purity 98%) of hexahydro-2-oxo-1,3-dibenzylthieno[3,4-d]imidazole-4-pentanoic acid, 277.68 g of mesitylene and 155.51 g of 96% by weight sulfuric acid was stirred for 2 hours at an inner temperature of 100° C., and kept. Then, to this was added 373.78 g of toluene and the mixture was stirred and left to separate the toluene layer which was removed. The sulfuric acid layer after removal of the toluene layer was added to 1242.05 g of a 11% aqueous sodium hydroxide solution, and to this was further added 3.61 g of activated carbon, and the mixture was stirred. To the filtrate after filtering the activated carbon was added 173.24 g of 35% hydrochloric acid and the pH of the mixture was controlled to 1, then, the inner temperature was lowered to 0° C., and crystals of precipitated hexahydro-2-oxo-1H-thieno[3,4-d]imidazole-4-pentanoic acid were filtrated. Amount obtained: 54.76 g (yield: 90.7%, purity: 94.2%).

Example 2

A mixture composed of 300.00 g (purity 98%) of hexahydro-2-oxo-1,3-dibenzylthieno[3,4-d]imidazole-4-pentanoic acid, 833.16 g of mesitylene, 304.52 g of acetic acid and 497.71 g of 96% by weight sulfuric acid was stirred for 8 hours at an inner temperature of 115° C., and kept. Then, to this was added 1121.03 g of toluene and the mixture was stirred and left, then, the toluene layer was removed. The sulfuric acid layer after removal of the toluene layer was added to 4601.17 g of a 14% aqueous sodium hydroxide solution, and to this was further added 10.83 g of activated carbon, and the mixture was stirred. To the filtrate after filtering the activated carbon was added 887.17 g of 35% hydrochloric acid and the pH of the mixture was controlled to 1, then, the inner temperature was lowered to 0° C., and crystals of precipitated hexahydro-2-oxo-1H-thieno[3,4-d]imidazole-4-pentanoic acid were filtrated. Amount obtained: 164.87 g (yield: 91.6%, purity: 94.1%).

Example 3

A mixture composed of 25.03 g (purity 98%) of hexahydro-2-oxo-1,3-dibenzylthieno[3,4-d]imidazole-4-pentanoic acid, 69.49 g of mesitylene, 5.32 g of formic acid and 38.59 g of 96% sulfuric acid was stirred for 2 hours at an inner temperature of 100° C., and kept. Then, to this was added 93.58 g of toluene and the mixture was stirred and left to separate the toluene layer which was removed. 300.56 g of water was added to the sulfuric acid layer after removal of the toluene layer at 80° C. and cooled to 0° C. Precipitated crystals of hexahydro-2-oxo-1H-thieno[3,4-d]imidazole-4-pentanoic acid were collected by filtration. Amount obtained: 12.81 g (yield: 90.6%, purity: 99.6%).

Example 4

A mixture of 50.07 g (purity 98%) of hexahydro-2-oxo-1,3-dibenzylthieno[3,4-d]imidazole-4-pentanoic acid, 138.85 g of mesitylene, 36.24 g of formic acid and 77.15 g of 96% sulfuric acid was stirred for 2 hours at an inner temperature of 115° C., and kept. Then, to this was added 186.53 g of toluene and the mixture was stirred and left, then, the toluene layer was removed. To the sulfuric acid layer after removal of the toluene layer was added 60.08 g of acetic acid. To this solution was added 600.98 g of water at 80° C. Then the mixture was cooled to 0° C. and precipitated crystals of hexahydro-2-oxo-1H-thieno[3,4-d]imidazole-4-pentanoic acid were collected by filtration. Amount obtained: 27.25 g (yield: 91.7%, purity: 95.0%).

Example 5

A mixture of 50.02 g (purity 98%) of hexahydro-2-oxo-1,3-dibenzylthieno[3,4-d]imidazole-4-pentanoic acid, 138.97 g of mesitylene, 10.65 g of formic acid and 45.36 g of 96% sulfuric acid was stirred for 4 hours at an inner temperature of 120° C., and kept. After removal of the mesitylene layer, 186.97 g of toluene was added thereto and stirred, allowed to settle and the toluene layer was separated. After removal of the toluene layer, to the resulting sulfuric acid layer was added 60.03 g of acetic acid and further added 599.89 g of water at 80° C. and cooled to 0° C. Precipitated crystals of hexahydro-2-oxo-1H-thieno[3,4-d]imidazole-4-pentanoic acid were collected by filtration. Amount obtained: 27.91 g (yield: 91.2%, purity: 92.2%).

Example 6

A mixture of 50.00 g (purity 98%) of hexahydro-2-oxo-1,3-dibenzylthieno[3,4-d]imidazole-4-pentanoic acid, 139.03 g of mesitylene and 77.11 g of 96% sulfuric acid was stirred for 2 hours at an inner temperature of 100° C. After removal of the mesitylene layer, 186.95 g of toluene was added thereto and stirred, allowed to settle and the toluene layer was separated. After removal of the toluene layer, to the resulting sulfuric acid layer was added 60.35 g of acetic acid and further added 600.38 g of water at 80° C. and then cooled to 0° C. Precipitated crystals of hexahydro-2-oxo-1H-thieno[3,4-d]imidazole-4-pentanoic acid were collected by filtration. Amount obtained: 26.58 g (yield: 93.5%, purity: 99.2%).

Example 7

A mixture of 50.10 g (purity 98%) of hexahydro-2-oxo-1,3-dibenzylthieno[3,4-d]imidazole-4-pentanoic acid, 139.00 g of mesitylene and 56.78 g of 96% sulfuric acid was stirred for 5 hours at an inner temperature of 100° C. After removal of the mesitylene layer, 186.82 g of toluene was added thereto and stirred, allowed to settle and the toluene layer was separated. After removal of the toluene layer, to the resulting sulfuric acid layer was added 60.63 g of acetic acid and further added 600.66 g of water at 80° C. and then cooled to 0° C. Precipitated crystals of hexahydro-2-oxo-1H-thieno[3,4-d]imidazole-4-pentanoic acid were collected by filtration. Amount obtained: 26.73 g (yield: 92.2%, purity: 97.5%).

Example 8

A mixture of 25.03 g (purity 98%) of hexahydro-2-oxo-1,3-dibenzylthieno[3,4-d]imidazole-4-pentanoic acid, 69.41 g of mesitylene and 38.60 g of 96% sulfuric acid was stirred for 2.5 hours at an inner temperature of 100° C. After removal of the mesitylene layer, 93.52 g of toluene was added thereto and stirred, allowed to settle and the toluene layer was separated. After removal of the toluene layer, to the resulting sulfuric acid layer was added 300.00 g of water at 80° C. and then cooled to 0° C. Precipitated crystals of hexahydro-2-oxo-1H-thieno[3,4-d]imidazole-4-pentanoic acid were collected by filtration. Amount obtained: 13.74 g (yield: 93.9%, purity: 96.8%).

Example 9

A mixture of 25.06 g (purity 98%) of hexahydro-2-oxo-1,3-dibenzylthieno[3,4-d]imidazole-4-pentanoic acid, 69.77 g of mesitylene and 38.86 g of 96% sulfuric acid was stirred for 2 hours at an inner temperature of 100° C. After removal of the mesitylene layer, 94.08 g of toluene was added thereto and stirred, allowed to settle and the toluene layer was separated. After removal of the toluene layer, to the resulting sulfuric acid layer was added 300.00 g of water at 80° C. and then cooled to 0° C. Precipitated crystals of hexahydro-2-oxo-1H-thieno[3,4-d]imidazole-4-pentanoic acid were collected by filtration. Amount obtained: 13.14 g (yield: 92.9%, purity: 99.7%).

Example 10

A mixture of 77.31 g (purity 98%) of hexahydro-2-oxo-1,3-dibenzylthieno[3,4-d]imidazole-4-pentanoic acid, 214.67 g of mesitylene and 119.36 g of 96% sulfuric acid was stirred for 2 hours at an inner temperature of 100° C. After removal of the mesitylene layer, the separated mesitylene layer was subjected to distillation while gradually reducing pressure from atmospheric pressure to 0.3 kPa(2 Torr) at 80° C. to recover 135.5 g of mesitylene. Recovery ratio of mesitylene was 63%.

A mixture of 25.09 g (purity 98%) of hexahydro-2-oxo-1,3-dibenzylthieno[3,4-d]imidazole-4-pentanoic acid, 69.46 g of mesitylene recovered as above and 38.52 g of 96% sulfuric acid was stirred for 3 hours at an inner temperature of 100° C. After removal of the mesitylene layer, to the resulting sulfuric acid layer was added 300.56 g of water at 80° C. and then cooled to 0° C. Precipitated crystals of hexahydro-2-oxo-1H-thieno[3,4-d]imidazole-4-pentanoic acid were collected by filtration. Amount obtained: 13.45 g (yield: 93.2%, purity: 97.9%).

What is claimed is:

1. A method for producing hexahydro-2-oxo-1H-thieno[3,4-d]imidazole-4-pentanoic acid of the formula (2):

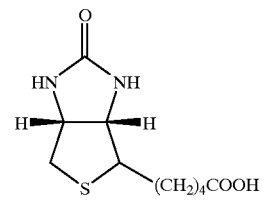

(2)

which method comprises contacting a compound of the formula (1):

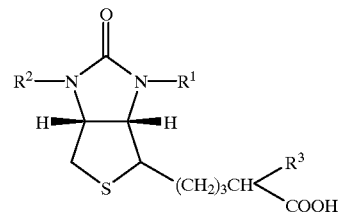

(1)

wherein $R^1$ and $R^2$ represent a hydrogen atom or a benzyl group, provided that $R^1$ and $R^2$ do not simultaneously represent a hydrogen atom, and $R^3$ represents a hydrogen atom or a carboxyl group, with sulfuric acid having a concentration of 90% by weight or more in the presence of an aromatic hydrocarbon.

2. The method according to claim 1, wherein the aromatic hydrocarbon is an alkylbenzene.

3. The method according to claim 1 or 2, wherein the alkylbenzene is mesitylene.

4. The method according to claim 3, wherein the treatment temperature is 50 to 120° C.

5. The method according to claim 1 or 2, wherein the sulfuric acid is present in an amount of from 1 to 20 moles per mol of a compound of the formula (1).

6. The method according to claim 1 or 2, wherein the aromatic hydrocarbon is present in an amount of from 2 to 30 moles per mol of the compound of the formula (1).

7. The method according to claim 1 or 2, wherein said compound of the formula (1) has the same stereochemistry as D-biotin.

* * * * *